(12) United States Patent
Nieuwenhuis

(10) Patent No.: US 8,449,833 B2
(45) Date of Patent: May 28, 2013

(54) FRUSTRATED TOTAL INTERNAL REFLECTION BIOSENSOR CARTRIDGE

(75) Inventor: Jeroen Hans Nieuwenhuis, Waalre (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 268 days.

(21) Appl. No.: 12/739,174

(22) PCT Filed: Oct. 24, 2008

(86) PCT No.: PCT/IB2008/054395
§ 371 (c)(1),
(2), (4) Date: Apr. 22, 2010

(87) PCT Pub. No.: WO2009/057024
PCT Pub. Date: May 7, 2009

(65) Prior Publication Data
US 2010/0310423 A1    Dec. 9, 2010

(30) Foreign Application Priority Data
Oct. 29, 2007   (EP) .................................. 07119528

(51) Int. Cl.
*G01N 21/75*   (2006.01)
*G01N 33/543*   (2006.01)
*G01N 21/77*   (2006.01)
*G01N 27/327*   (2006.01)

(52) U.S. Cl.
CPC ...... *G01N 33/54366* (2013.01); *G01N 21/7703* (2013.01); *G01N 27/3271* (2013.01); *G01N 27/3272* (2013.01); *G01N 33/5438* (2013.01); *Y10S 436/805* (2013.01); *Y10S 436/809* (2013.01)
USPC ............... 422/402; 422/52; 422/63; 422/64; 422/82.05; 422/82.06; 422/82.08; 422/82.09; 422/82.11; 422/400; 422/401; 422/407; 422/425; 422/426; 422/429; 422/500; 422/501; 422/502; 422/503; 422/504; 436/149; 436/164; 436/165; 436/166; 436/172; 436/174; 436/180; 436/518; 436/524; 436/805; 436/809; 435/164; 435/165; 435/283.1; 435/287.1; 435/287.2; 435/4; 435/5; 435/7.2; 435/7.9; 204/403.01; 222/1; 359/321; 369/112.07

(58) Field of Classification Search
CPC .......... G01N 33/54366; G01N 21/7703; G01N 27/3271; G01N 27/3272; G01N 33/5438
USPC ............... 422/102, 52, 82.05, 82.08, 82.09, 422/82.11, 99, 407, 63, 64, 68.1, 82.06, 400, 422/401, 402, 425, 426, 429, 500, 501, 502, 422/503, 504; 435/164, 165, 283.1, 287.1, 435/287.2, 4, 5, 7.2, 7.9; 436/149, 164, 172, 436/174, 518, 805, 809, 165, 166, 180, 524; 204/403.01; 222/1; 359/321; 369/112.07; 382/133; 430/290, 321; 506/3, 39, 9; 526/318.2, 319; 250/458.1, 559.29, 574; 356/128, 244, 246, 300, 326, 414, 416, 445, 356/369; 385/12, 129, 130, 14, 37
See application file for complete search history.

(56) References Cited

U.S. PATENT DOCUMENTS 4,849,340 A    7/1989   Oberhardt
5,962,218 A *  10/1999  Leland et al. ................. 435/6.11
(Continued)

FOREIGN PATENT DOCUMENTS

EP    0949002 A2    10/1999
WO    0208762 A1    1/2002
(Continued)

*Primary Examiner* — Dennis M White

(57) ABSTRACT

The present invention provides a biosensor cartridge (11) comprising a bottom portion (1) with a well (2) adapted to accommodate a liquid sample and a cover portion (3) for closing said well (2). The well (2) has a sensor surface (4). The bottom portion (1) is adapted for allowing light to enter along a first optical path (5), to be reflected at the sensor surface (4) and to exit along a second optical path (6). The invention further relates to a method of manufacturing such a cartridge (11).

18 Claims, 4 Drawing Sheets

U.S. PATENT DOCUMENTS

| | | |
|---|---|---|
| 6,020,209 A | 2/2000 | Narang et al. |
| 6,137,117 A | 10/2000 | Feldstein et al. |
| 6,207,000 B1 * | 3/2001 | Schwobel et al. ............ 156/248 |
| 6,242,267 B1 | 6/2001 | Herron et al. |
| 6,607,701 B1 | 8/2003 | Jansson et al. |
| 7,022,515 B2 | 4/2006 | Herron et al. |
| 7,233,391 B2 | 6/2007 | Schermer et al. |
| 2004/0228764 A1 | 11/2004 | Stephens et al. |
| 2005/0112028 A1 | 5/2005 | Ohtsuka et al. |
| 2005/0179901 A1 | 8/2005 | Ostlin et al. |
| 2006/0238766 A1 | 10/2006 | Polwart |
| 2006/0257956 A1 | 11/2006 | Basset et al. |
| 2007/0072287 A1 | 3/2007 | Morisette et al. |

FOREIGN PATENT DOCUMENTS

| | | |
|---|---|---|
| WO | 2006120656 A1 | 11/2006 |
| WO | WO 2007073107 A1 * | 6/2007 |

* cited by examiner

FRUSTRATED TOTAL INTERNAL REFLECTION BIOSENSOR CARTRIDGE

FIELD OF THE INVENTION

The invention relates to a cartridge for use in a Frustrated Total Internal Reflection (FTIR) biosensor and to a method of manufacturing such a cartridge.

BACKGROUND OF THE INVENTION

The demand for biosensors is increasingly growing these days. Usually, biosensors allow for the detection of a given specific molecule within an analyte, wherein the amount of said molecule is typically small. For example, one may measure the amount of drugs or cardiac markers within saliva or blood. Therefore, target particles, for example super-paramagnetic label beads, are used which bind to a specific binding site or spot only, if the molecule to be detected is present within the analyte. One known technique to detect these label particles bound to the binding spot is FTIR. Therein, light is coupled into the sample at an angle of total internal reflection. If no particles are present close to the sample surface, the light is completely reflected. If, however, label particles are bound to said surface, the condition of total internal reflection is violated, a portion of the light is scattered into the sample and thus the amount of light reflected by the surface is decreased. By measuring the intensity of the reflected light with an optical detector, it is possible to estimate the amount of particles bound to the surface. This allows for an estimate of the amount of the specific molecules of interest present within the analyte or sample.

Since this technique is expected to become a standard tool in biosensing, there is a growing need for cartridges which may be used for FTIR. Since bio sensors based on immunoreactions need to be disposable, because the biochemical material inside the cartridge is altered during an experiment, there is, in particular, a need for cheap disposable cartridges for FTIR or other detection methods.

SUMMARY OF THE INVENTION

It is therefore an object of the present invention to provide an improved cartridge for biosensors. This object is achieved with the features of the independent claims.

The present invention provides a cartridge for a biosensor comprising a bottom portion with a well adapted to accommodate a sample, said well having a sensor surface, and a cover portion for closing said well, wherein said bottom portion is adapted for allowing light to enter along a first optical path, to be reflected at the sensor surface and to exit along a second optical path, wherein the cover portion comprises a tape or foil. Optionally, a layer of adhesive may be provided between bottom portion and cover portion. It may be advantageous, though, if the layer of adhesive is interrupted at or above the well. Thus, any interaction between the sample within the well and the adhesive is prevented.

The present invention also provides a method of manufacturing a cartridge comprising the following steps:
a) providing a bottom portion of a first material with a well adapted to accommodate a sample;
b) providing a roll or sheet of a second material;
c) applying a reagent and/or label particles to specific sites on the roll or sheet;
d) cutting the roll or sheet into cover portions, wherein each cover portion contains the reagent and/or label particles; and
e) attaching the cover portion to the bottom portion such that the reagent and/or label particles are enclosed by the well.

The bottom portion of said cartridge may be made of plastics, preferably moulded. Optionally, a layer of adhesive may be provided between bottom portion and cover portion. It may be advantageous, though, if the layer of adhesive is interrupted at or above the well. Thus, any interaction between the sample within the well and the adhesive is prevented.

In a preferred embodiment, the well comprises a channel. The well may have a larger width and depth than the channel, but it is also conceivable that the whole well consists of a channel. The cartridge further comprises at least one passage or opening for supplying the sample into the well. That may be, e.g., a groove in the bottom portion or a hole in the cover portion. It is also conceivable that the channel is open at one or both end(s).

According to a preferred embodiment, the bottom portion of the cartridge comprises a recess for accommodating a means for providing a magnetic field, e.g., a coil. Furthermore, the bottom portion may comprise an optical input surface and an optical output surface within first and second optical paths, respectively. Preferably, these surfaces are perpendicular to the first and second optical paths.

Furthermore, the well may contain a reagent or a combination of several reagents and label particles. In a preferred embodiment, these reagents are situated at specific binding spots of the sensor surface. According to another embodiment, the reagents and/or the label particles are provided on the cover portion. For example, they may be printed onto a film forming the cover portion.

The label particles may be coated with capture molecules and may further comprise magnetic particles. It is, for instance, advantageous, if the label particles are super-paramagnetic.

The present invention also refers to a method of manufacturing a cartridge as described above. According to said method, a bottom portion of a first material with a well adapted to accommodate a sample is provided. Furthermore, a roll or sheet of a second material is provided. Then a reagent and/or label particles are applied to specific sites on the roll or sheet and the roll or sheet is cut into cover portions, wherein each cover portion contains the reagent and/or label particles. Finally, the cover portion is attached to the bottom portion such that the reagent and/or label particles are enclosed by the well. Optionally, said method may comprise the step of applying a layer of adhesive onto the bottom portion and/or the roll or sheet of second material.

These and other aspects of the invention will be apparent from and elucidated with reference to the embodiment(s) described hereinafter.

DETAILED DESCRIPTION OF EMBODIMENTS

Figure 1A:
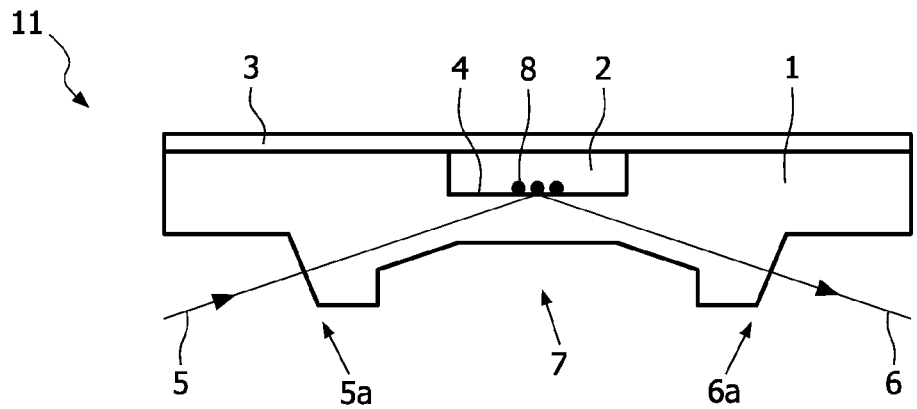
FIG. 1a schematically shows a cross section of a cartridge according to the present invention.

FIG. 1a schematically shows a side view of a cross section of a cartridge 11 as an example of the present invention. The cartridge 11 comprises a bottom portion 1 with a well 2 and a cover portion 3. The well 2 is adapted to be filled with a sample and is closed or covered by cover portion 3. At the bottom, well 2 is confined by sensor surface 4. Light enters the bottom portion 1 at optical input surface 5a along a first optical path 5, is reflected at said sensor surface 4 and exits bottom portion 1 at optical output surface 6a along a second optical path 6. Bottom portion 1 further forms a recess 7, which is adapted to accommodate a means for providing a magnetic field to the end of exerting forces on magnetic label particles 8. This is done to achieve a binding between a reagent and the label particles 8, the so called actuation process. The well 2 contains a reagent (not shown) and the label particles 8.

Figure 1B:
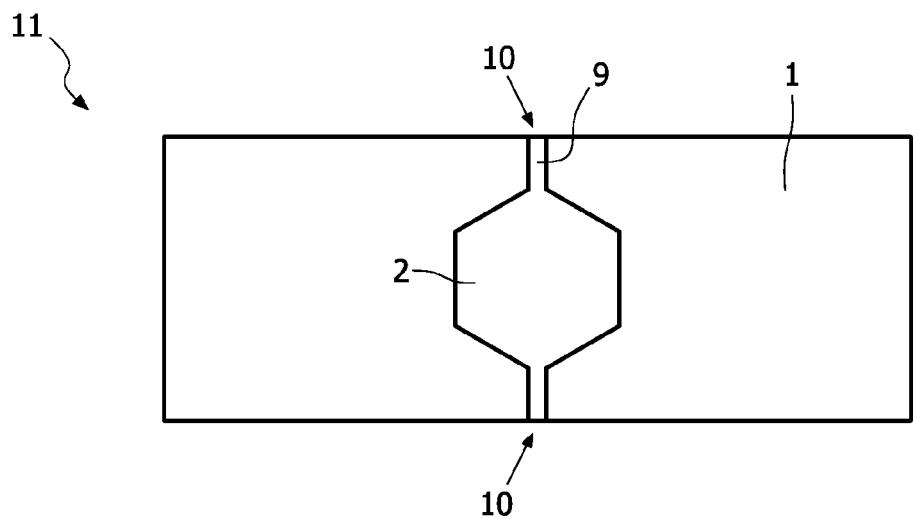
FIG. 1b schematically shows a top view of the bottom portion of a cartridge according to the present invention.
Figure 1C:
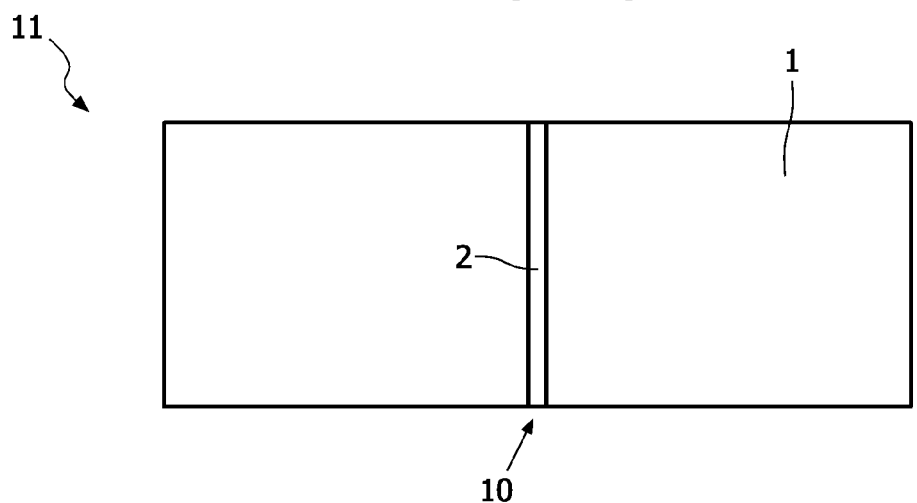
FIG. 1c schematically shows a top view of the bottom portion of another cartridge according to the present invention.

As can be seen in FIG. 1b schematically showing a top view of the bottom portion 1 of the cartridge 11, well 2 may further comprise a channel 9. The whole well 2 may also consist of the channel 9 as shown in FIG. 1c. At the ends, channel 9 comprises a passage or opening 10 for supplying the sample into the well 2. That may be, e.g., a groove in the bottom portion as depicted in FIGS. 1b and 1c or a hole in the cover portion 3.

Filling of the well 2 may thus be achieved by capillary forces: If a droplet of a sample touches passage or opening 10, it is dragged into the well 2, if the dimensions of channel 9 are chosen small enough. In that case, it is obviously necessary to provide a second passage or opening 10 to allow for air leaving the well 2. However, it may also be possible to fill the well 2 by applying a pressure, e.g., with a syringe or the like.

Figure 2:
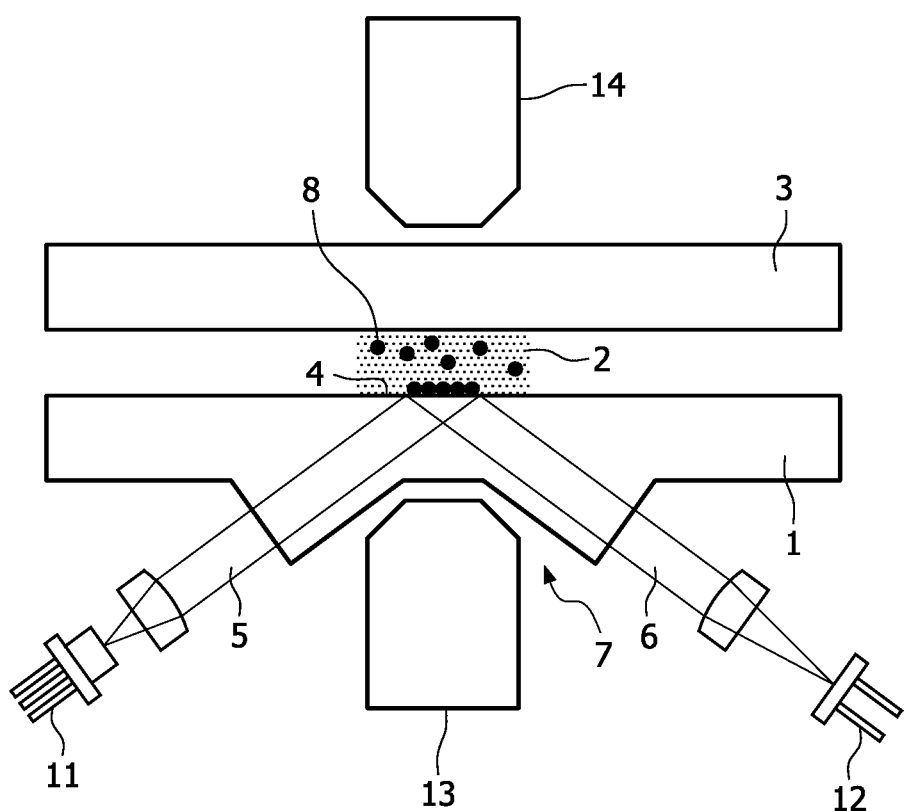
FIG. 2 schematically shows the functional principle of FTIR.

FIG. 2 schematically shows the functional principle of FTIR as an example of an detection method used with the cartridge 11. Once well 2 is filled or supplied with a liquid sample to be detected as described above, label particles 8, which have been supplied in a dry form, redisperse into solution. Using magnet 13, super-paramagnetic label particles 8 may be accelerated towards sensor surface 4, where they may bind to the surface if the specific molecule to be detected is present in the sample. After some time sufficient for binding, magnet 14 may be used in order to remove label particles 8, which are not bound to sensor surface 4, from said surface. After this 'washing' step, sensor surface 4 is illuminated with laser or LED 11. The light is reflected at sensor surface 4 and detected by detector 12, which may be a photo diode or a CCD camera. Typically, the optical element or detector 12 is read-out continuously during the assay process, the binding process described above, and the progress of the binding process is monitored. However, alternatively an image may be obtained before the assay and one image after the assay and the differences may then be compared. The optical path 5 of incoming light is chosen such that the condition of total internal reflection is fulfilled. In that case, an evanescent optical field is generated, which penetrates typically only 50-100 nm into well 2. Thus, only if label particles 8 are that close to the sensor surface 4, the evanescent field is disturbed leading to a decrease in reflected intensity.

The present invention also refers to a method of manufacturing a cartridge 11 as described above. According to said method, a bottom portion 1 of a first material with a well 2 adapted to accommodate a sample is provided. Said first material is preferably a plastic material, for example polystyrene, polycarbonate, cyclo-olefin-polymer (COP or Zeonex) or PET (Polyethylenterephthalat). The bottom portion 1 may be moulded, e.g., injection-moulded, with said first material. However, other techniques of forming the bottom portion 1 may be used as well.

Figure 3A:
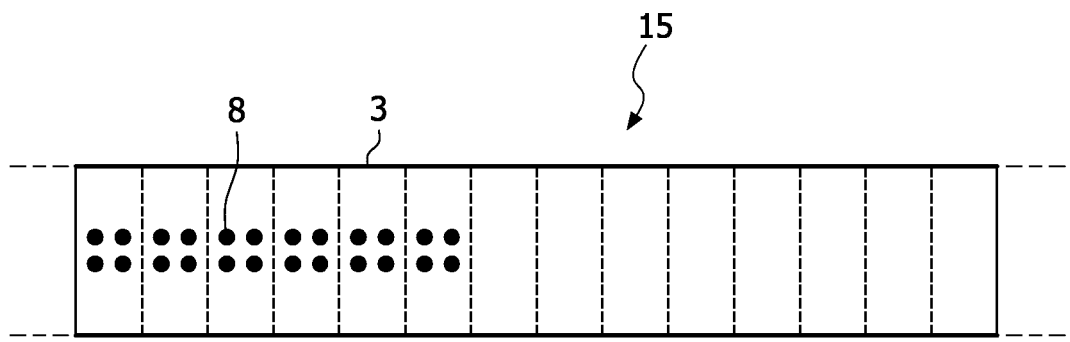
FIG. 3a schematically shows a roll of material for use as cover portions.
Figure 3B:
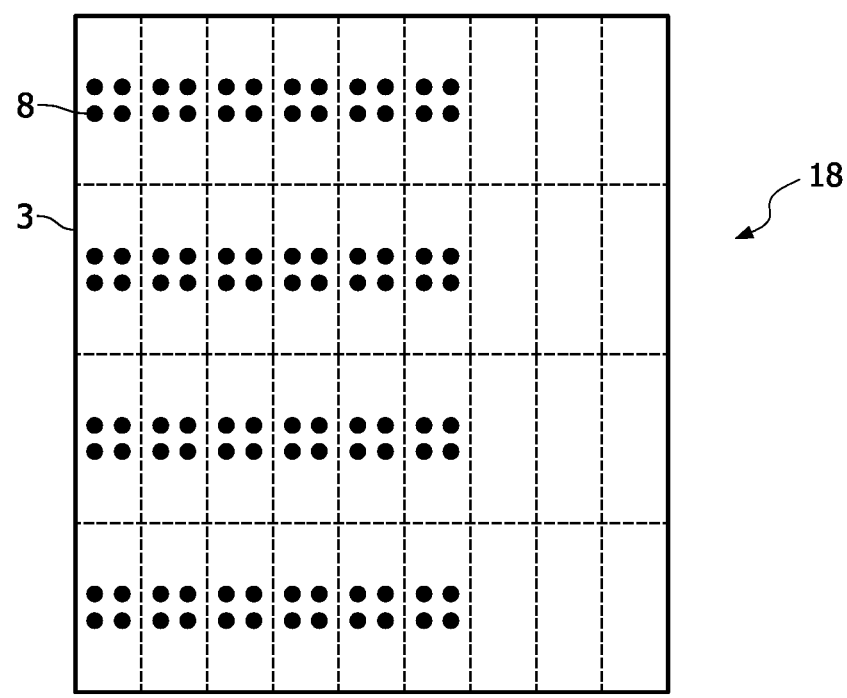
FIG. 3b schematically shows a sheet of material for use as cover portions.

Furthermore, a roll 15 or sheet 18 of a second material is provided, as shown in FIG. 3a depicting the roll 15 and 3b depicting the sheet 18. Said roll 15 or sheet 18 may comprise a foil or tape from, e.g., polyester. If the roll 15 or sheet 18 consists of a foil, a further layer of adhesive may be applied to adhere the foil to the cartridge 11. In some embodiments, said adhesive may only partially cover the roll 15 or sheet 18.

Then a reagent and/or label particles 8 are applied to specific sites on the roll 15 or sheet 18 and the roll 15 or sheet 18 is cut into cover portions 3, wherein each cover portion 3 contains the reagent and/or label particles 8. Finally, the cover portion 3 is attached to the bottom portion 1 of the cartridge 11 such that the reagent and/or label particles 8 are enclosed by the well 2. If no adhesive is present on the roll 15 or sheet 16 other bonding techniques may be used for attaching cover portion 3 to bottom portion 1, for example thermal bonding techniques such as ultra-sonic welding or laser-welding may be used.

The reagent may alternatively be supplied to the sensor surface 4 of well 2. It is, in particular, preferred to provide several specific binding spots with reagents on the sensor surface 4. The reagents of different binding spots may also differ from each other in order to provide specific binding spots for different molecules in the sample to be analyzed. These molecules may be, e.g., anti-bodies or conjugated analyte molecules (e.g. in case of an inhibition assay).

Figure 4:
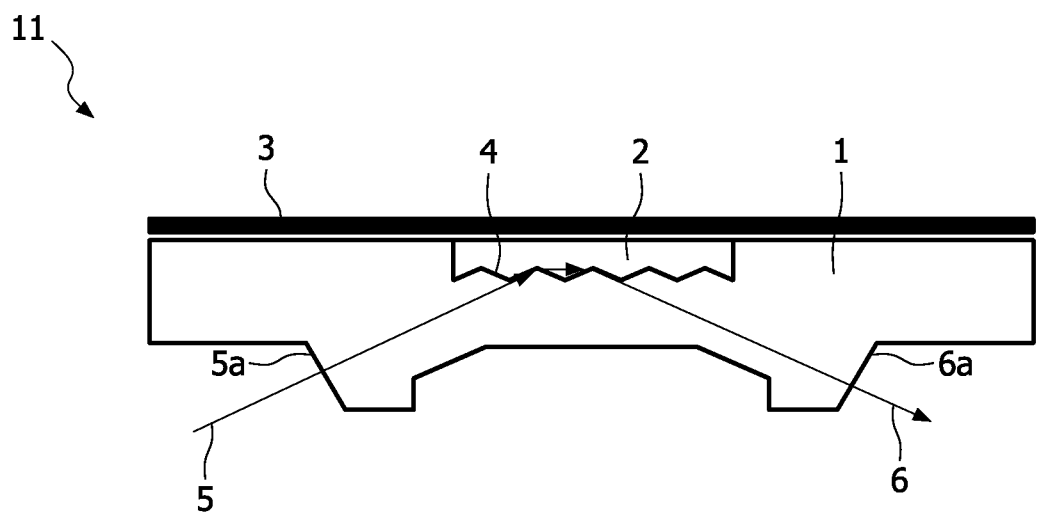
FIG. 4 schematically shows a side view of an alternative structure of the cartridge.

FIG. 4 shows another schematic cross-sectional side view of an example of the cartridge 11 similar to FIG. 1a. The bottom portion 1 is similar to the bottom portion 1 of FIG. 1a, for instance moulded from plastics. The optical input surface 5a for input of light along the optical path 5 and the optical output surface 6a for output of light along the optical path 5 are provided. The well 2 formed in the bottom portion 1 is covered by the cover portion 3 and thereby imbedded forming a closed space. The difference of example of FIG. 4 to example of FIG. 1a is that the sensor surface 4 is not an essentially flat surface but has a jagged structure. At least one wedge formed structure is provided at the sensor surface 4 leading to a different course of light impinging at the sensor surface 4. Typically, the course of light is then a reflection at a declining facet, whereby most of the light transmits the facet, the light being reflected to the opposite inclining facet, whereby the declining facet and the inclining facet of the sensor surface 4 form a recess like the equal sides of a isosceles triangle. From the second declining facet the light is again reflected away from the well 2 to the direction of the optical output surface 6a along the second optical path 6 as shown in FIG. 4. The sample to be detected with the reagents and/or label particles 8 (not shown here) again are situated at the sensor surface 4, essentially between the wedge shaped facets. Detection principle is that light is blocked essentially by label particles 8 bound to molecules of the sample. By calculating the difference of incoming light along the first optical path 5 and outcoming light along the second optical path 6 the amount of molecules in the sample can be concluded.

An important aspect of the invention is, as described, that the cartridge 11 is build from a bottom portion 1 comprising the well 2 to contain the sample and a single cover portion 3 covering the well 2 which is a tape or foil. This structure makes the cartridge 11 cheap and useful as a disposable part in biosensors. A tape in this connection is defined as being adhesive at one side and formed as a flat and flexible body from different common materials. A foil in this connection is defined as being not adhesive and formed as a flat and flexible body from different common materials. In the latter case a layer of adhesive is provided between the bottom portion 1 and the foil. Tapes and foils are applied to the bottom portion 1 in stripes which are cut at the edges of the bottom portion 1.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A device, comprising
   a bottom portion having formed therein a well configured to accommodate a sample, said bottom portion including a sensor surface as a bottom interior surface of the well, the bottom interior surface of the well having a jagged structure defining at least one recess in a shape of an isosceles triangle; and
   a cover portion for closing said well, disposed on an opposite side of the well from the sensor surface, wherein said bottom portion is adapted for allowing light to enter along a first optical path, to be passed to the sensor surface and to exit along a second optical path, wherein the cover portion comprises a tape or foil.

2. The device of claim 1, wherein the bottom portion is made of plastics and/or the bottom portion is moulded.

3. The device of claim 1, wherein the well comprises a channel and the well contains a reagent or a combination of several reagents and/or label particles, wherein the reagent or the combination of several reagents is situated at specific binding spots of the sensor surface.

4. The device of claim 1, further comprising a layer of adhesive between the bottom portion and the cover portion which is interrupted at the well.

5. The device of claim 3, wherein the label particles are coated with capture molecules.

6. The device of claim 5, wherein the label particles comprise magnetic particles.

7. The device of claim 1, further comprising at least one passage or opening for supplying the sample into the well.

8. The device of claim 7, wherein the at least one passage or opening is a groove in the bottom portion.

9. The device of claim 1, wherein the bottom portion comprises an optical input surface and an optical output surface within the first and second optical paths, respectively.

10. The device of claim 9, wherein the optical input and optical output surfaces are perpendicular to the first and second optical paths, respectively.

11. The device of claim 1, wherein the cover portion contains a print-label with product information and/or identification.

12. A method of manufacturing a cartridge, comprising:
   a) providing a bottom portion of a first material, the bottom portion having formed therein a well configured to accommodate a sample, the bottom portion including a sensor surface as a bottom interior surface of the well, wherein the bottom interior surface has a jagged structure defining at least one recess in a shape of an isosceles triangle;
   b) providing a roll or sheet of a second material;
   c) applying a reagent and/or label particles to specific sites on the roll or sheet;
   d) cutting the roll or sheet having the reagent and/or label particles applied at specific sites thereto into cover portions, wherein each cover portion contains the reagent and/or label particles (8); and
   e) attaching the cover portion to the bottom portion such that the reagent and/or label particles are enclosed by the well and the cover portion.

13. The method of claim 12, further comprising applying a layer of adhesive onto the bottom portion and/or the roll or sheet of second material.

14. The device of claim 1, further comprising a magnet disposed so as to provide a magnetic field within the well.

15. The device of claim 14, wherein the bottom portion has a cavity formed therein on a side of the bottom portion which is opposite the cover portion, and wherein at least a portion of the magnet is disposed within the cavity.

16. The device of claim 15, wherein the bottom portion has an optical input surface in the first optical path and has an optical output surface in the second optical path, and wherein the cavity is disposed between the optical input surface and the optical output surface.

17. The device of claim 15, further comprising a second magnet disposed on an opposite side of the cover portion as the first magnet.

18. The device of claim 1, wherein the cover portion comprises a single unitary structure covering the entire well.

* * * * *